United States Patent [19]

Ozretich

[11] 3,930,835

[45] *Jan. 6, 1976

[54] PESTICIDAL COMPOSITIONS AND METHODS EMPLOYING SUBSTITUTED OXIRANE COMPOUNDS

[75] Inventor: Thomas M. Ozretich, Vancouver, Wash.

[73] Assignee: The Dow Chemical Company, Midland, Mich.

[ * ] Notice: The portion of the term of this patent subsequent to Mar. 6, 1990, has been disclaimed.

[22] Filed: Oct. 2, 1972

[21] Appl. No.: 294,329

Related U.S. Application Data

[63] Continuation-in-part of Ser. No. 61,848, Aug. 6, 1970, abandoned.

[52] U.S. Cl................ 71/88; 260/348 R; 424/278
[51] Int. Cl.²......................................... A01N 9/28
[58] Field of Search..................... 71/88; 260/348 R

[56] References Cited
UNITED STATES PATENTS

| | | | |
|---|---|---|---|
| 2,939,872 | 6/1960 | Hudson | 260/348 |
| 2,993,058 | 7/1961 | Hudson | 260/348 |
| 3,166,398 | 1/1965 | Walworth et al. | 71/88 |
| 3,183,074 | 5/1965 | Walworth et al. | 71/88 |
| 3,798,254 | 3/1974 | Phillips | 71/88 |

FOREIGN PATENTS OR APPLICATIONS

| | | |
|---|---|---|
| 527,462 | 7/1956 | Canada |

*Primary Examiner*—Lewis Gotts
*Assistant Examiner*—Catherine L. Mills
*Attorney, Agent, or Firm*—Gary D. Street; Edward E. Schilling

[57] ABSTRACT

Disclosed herein are substituted oxirane compounds corresponding to the formula

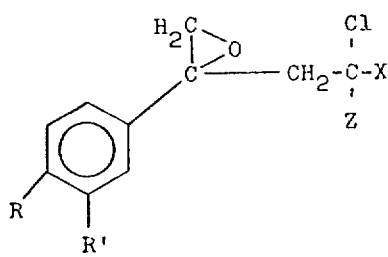

wherein X represents halogen; Z represents hydrogen, halogen, cyano or lower alkyl; R and R' each independently represent hydrogen, halogen, cyano, nitro, alkoxy, trifluoromethyl, benzyloxy or lower alkyl, with the proviso that when R' is hydrogen, R is other than hydrogen. The compounds are especially useful as pesticides in preventing germination of undesired plant seeds and controlling noxious weeds and fungal organisms and can be formulated to provide pesticidal compositions.

33 Claims, No Drawings

PESTICIDAL COMPOSITIONS AND METHODS EMPLOYING SUBSTITUTED OXIRANE COMPOUNDS

CROSS-REFERENCE TO RELATED APPLICATION

The present application is a continuation-in-part of my copending application Ser. No. 61,848, filed Aug. 6, 1970, now abandoned.

BACKGROUND OF THE INVENTION

In recent years, the use of chemicals for controlling various biological forms has found widespread acceptance among many people. This is especially true among agriculturalists interested in controlling fungal and terrestrial plants. For example, chemical compositions have previously been applied to the soil or to the foliage of fully developed plants, thereby destroying certain types of plants in a selective manner and allowing others to continue their growth in a more favorable environment. This type of control, enabling certain plants to grow freely unhampered by competing noxious plants, has also been achieved by the application of chemical compositions to the soil, which chemical compositions either prevent germination of undesirable seeds or destroy the emerging seedlings immediately after germination. Other dangers confronting plant growth and crop yields occur in the form of plant diseases. These threats to desirable plant life have been lessened by the application of fungicides to the soil, foliage of the plants, and surrounding atmosphere.

Very effective control and protection of desirable plant life is therefore possible through the use of chemicals formulated to provide protection as selective herbicides and fungicides. However, all requirements for effectiveness and selectivity among pesticides have not been satisfied. There are still many demands to satisfy among agriculturalists and others, either for more effective pesticides with selectivity comparable to old pesticides, or for pesticides with a different selectivity.

SUMMARY OF THE INVENTION

This invention relates to pesticidal compositions and methods utilizing substituted oxirane compounds as active ingredients. According to the present invention, there are provided pesticidal compositions containing compounds of the formula:

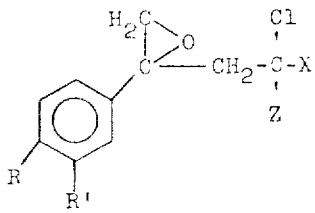

wherein X represents halogen; Z represents hydrogen, halogen, cyano or lower alkyl; R and R' each independently represent hydrogen, halogen, cyano, nitro, lower alkoxy, trifluoromethyl, benzyloxy or lower alkyl, with the proviso that when R' is hydrogen, R is other than hydrogen. An additional preferred class of compounds are those wherein R is hydrogen and R' is as previously defined. A preferred class of compounds are those wherein R and R' each independently represent hydrogen, halogen, nitro, lower alkoxy, trifluoromethyl or lower alkyl, with the proviso that when R' is hydrogen, R is other than hydrogen. A further preferred class of compounds are those wherein R and R' each independently represent hydrogen, halogen, trifluoromethyl or lower alkyl, with the proviso that when R' is hydrogen, R is other than hydrogen. An especially preferred class of compounds are those wherein R and R' each independently represent hydrogen, halogen or trifluoromethyl, with the proviso that when R' is hydrogen, R is other than hydrogen. A most preferred class of compounds are those where R represents hydrogen and R' represents halogen or trifluoromethyl.

Also provided herein are methods of controlling undesired fungal organisms and weed growth by application of the compounds of this invention. At low application rates certain of the compounds are useful as selective herbicides in desirable crops such as corn, cotton, soybeans, rice and the like.

As used herein, the term "lower alkyl" means saturated, monovalent aliphatic radicals, including straight and branched-chain radicals of from 1 to about 4 carbon atoms, as illustrated by, but not limited to, methyl, ethyl, propyl, isopropyl, butyl, sec.-butyl and the like. The term "lower alkoxy" includes straight and branched-chain radicals of from 1 to about 4 carbon atoms, as illustrated by, but not limited to, methoxy, ethoxy, propoxy, isopropoxy, butoxy, and the like. The term "halogen" represents bromine, chlorine, fluorine and iodine.

The substituted oxirane compounds of the present invention, hereinafter referred to as "oxirane" compounds, are generally oils or crystalline solids at room temperature which are soluble in the usual organic solvents such as, for example, 1,2-dichlorobenzene, methylene chloride, chloroform and the like. They are readily prepared by the reaction of a substituted styrene compound of the formula:

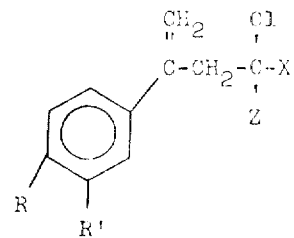

wherein R, R', X and Z are as hereinbefore defined, with a suitable percarboxylic acid reactant. Representative and suitable percarboxylic acids which can be employed in the preparation of the substituted oxirane compounds include, for example, peracetic acid, trifluoroperacetic acid, perbenzoic acid and the like. In the present invention, buffer solutions of the acid reactants are preferably employed and are prepared by the use of a buffer agent, such as, for example, sodium acetate, sodium benzoate and the like.

In carrying out the reaction, the percarboxylic acid reactant is added, dropwise or portionwise over a period of about 5–10 minutes, to the substituted styrene reactant. While the amounts of the reactants to be employed are not critical, the reaction generally consumes the reactants in the proportion of one mole of substituted styrene reactant to one or more moles of percarboxylic acid reactant. A suitable ratio of reactants is from about 1:1 to about 1:6 (substituted styrene:percarboxylic acid) and the employment of the reactants in a mole ratio of about 1:4 is preferred. The reaction is allowed to proceed at a temperature between about 20° and about 40°C. and is preferably maintained at room temperature. The pressure is not critical and is usually maintained at ambient atmospheric pressure. The reaction mass is maintained for a period of time sufficient to assure substantial completion of the reaction, generally from about 12 to about 20 hours or longer. Recovery of the product from the reaction mass is achieved by employing conventional procedures. Typically, the reaction mass is washed with water and neutralized with a sufficient amount of base, e.g., sodium carbonate, before being evaporated to dryness under reduced pressure.

The desirable properties of the present products are inherent in the pure compounds; when highly selective properties are to be relied, the purified compounds will be preferred. However, for many applications and especially wherein low cost is a major consideration, incompletely purified products can be employed since by-products of the reaction are often unobjectionable.

The substituted styrene compounds employed as starting materials can be prepared in accordance with known or analogous methods. See, for example, U.S. Pat. Nos. 3,391,203 and 3,336,401.

The following examples are presented to illustrate preparation of typical compounds employed in the invention, but the scope of the invention is not to be considered limited to the specific examples given.

EXAMPLE 1

A buffer solution of 40% peracetic acid (24 milliliters; 0.160 mole) and sodium acetate trihydrate (2.0 grams; 0.025 mole) was added dropwise with stirring to p-nitro-α-(2,2,2-trichloroethyl)styrene (12.0 grams; 0.043 mole) dissolved in 75 milliliters of methylene chloride. The addition was carried out over a period of about 5–10 minutes and at a temperature of about 25° to about 35°C. Following the addition, the reaction mass was maintained at a temperature of about 35°C. for a period of about 16 hours, in order to assure substantial completion of the reaction. Upon completion of the reaction, the reaction mass was washed with water to remove water-soluble impurities and neutralized with a sufficient amount of base, e.g., sodium carbonate. The reaction mass was again washed with water, dried over anhydrous sodium sulfate, and reduced to dryness by rotary evaporation. As a result of these operations, the 2-(p-nitrophenyl)-2-(2,2,2-trichloroethyl)oxirane product was recovered as a yellow crystalline solid. Recrystallization from chloroform gave the purified product as white plates having a melting point of 113°–114.5°C. Elemental analysis calculated for $C_{10}H_8Cl_3NO_3$ (percent): C, 40.5; H, 2.7; N, 4.7. Found (percent) C, 40.1; H, 2.7; N, 4.7.

EXAMPLES 2–33

Other representative products of the present invention, are prepared in accordance with the procedures reported in Example 1 above, using the respective corresponding substituted styrene reactant and percarboxylic acid reactant. These other representative products corresponding to the formula below are identified in the following table.

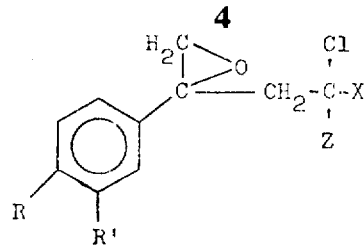

TABLE I

| Ex. No. | R | R' | X | Z | Characterizing Property |
|---|---|---|---|---|---|
| 2 | H | $NO_2$ | Cl | Cl | *M.W. 296.5 |
| 3 | H | Br | Cl | Cl | *$n_D^{25}$ 1.5735 (88% pure) |
| 4 | H | $CF_3$ | Cl | Cl | *B.P. 86–88°C. |
| 5 | Cl | Cl | Cl | Cl | B.P. 75°C. at 0.5 mm Hg |
| 6 | H | Br | Cl | $C_2H_5$ | M.W. 324 |
| 7 | H | Cl | Cl | Cl | $n_D^{25}$ 1.5604 (95% pure) |
| 8 | $NO_2$ | H | Cl | $C_4H_9$ | M.W. 318 |
| 9 | H | $CH_3$ | Cl | Cl | B.P. 97°C. |
| 10 | –CN | H | Cl | H | M.W. 242 |
| 11 | $CH_3O$ | H | Cl | Cl | M.W. 281.5 |
| 12 | H | $CH_3O$ | Cl | Cl | B.P. 98°C. |
| 13 | H | $CH_3O$ | F | –CN | M.W. 255.5 |
| 14 | H | $CH_3CH_2O$ | Cl | Cl | $n_D^{25}$ 1.5475 (90% pure) |
| 15 | $CH_3O$ | $CH_3O$ | Cl | $C_3H_7$ | M.W. 319 |
| 16 | H | $C_6H_5CH_2O$ | Cl | Cl | $n_D^{25}$ 1.5703 (61% pure) |
| 17 | $NO_2$ | $NO_2$ | Br | $C_2H_5$ | M.W. 379.5 |
| 18 | –CN | –CN | Cl | Cl | M.W. 301.5 |
| 19 | H | F | Cl | Cl | M.W. 269.5 |
| 20 | $C_3H_7$ | H | F | $C_2H_5$ | M.W. 270.5 |
| 21 | $C_4H_9$ | $C_4H_9$ | Cl | Cl | M.W. 363.5 |
| 22 | $CH_3$ | –CN | Cl | Cl | M.W. 290.5 |
| 23 | $NO_2$ | $C_2H_5$ | Cl | $C_2H_5$ | M.W. 318 |
| 24 | Br | Br | Cl | H | M.W. 375 |
| 25 | $CF_3$ | H | Cl | Cl | M.W. 319.5 |
| 26 | H | $CF_3$ | F | $C_3H_7$ | M.W. 310.5 |
| 27 | $C_4H_9O$ | H | Cl | Cl | M.W. 323.5 |
| 28 | $C_4H_9O$ | $C_4H_9O$ | Cl | Cl | M.W. 395.5 |
| 29 | Cl | H | Cl | Cl | B.P. 80°C. |
| 30 | Br | H | Cl | Cl | M.P. 43.5–44.5°C. |
| 31 | $C_2H_5$ | H | Cl | –CN | M.W. 270 |
| 32 | $NO_2$ | H | Cl | –CN | M.W. 287 |
| 33 | H | $CH_3O$ | Cl | –CN | M.W. 272 |

*M.W. = Molecular Weight
*B.P. = Boiling Point
*$n_D^{25}$ = Refractive Index
*M.P. = Melting Point Compounds of this invention are useful as pesticides. The most distinctive utility of the compounds is based upon their ability to inhibit the growth of objectionable plant life. This inhibition or herbicical activity may be demonstrated by contacting a plant structure with the subject compounds, which may take place either pre-emergently or on established plants. Pre-emergence application may be accomplished in either of two ways — by application of the compounds to the surface of the soil or by incorporation of the compounds into the surface layer of soil. In addition to herbicidal activity, some of the compounds of this invention possess activity as fungicides. Some of the compounds possess multiple activity in two or more of the above mentioned areas. Hence the user may benefit from the application of these compounds in a dual or multiple manner, depending upon which compound or mixture of compounds is selected. Accordingly, the term pesticidal activity refers to a toxic activity in one or more of the above areas of herbicidal or fungicidal activity.

In particular, it has been discovered that undesirable plants and fungal organisms can be controlled by contacting such plants or organisms and/or their habitats with compositions containing an effective growth-controlling amount of at least one of the oxirane compounds disclosed herein. Complete control and kill of various fungal organisms is obtained when such organisms are contacted with compositions containing at least one of the oxirane compounds in dosages sufficient to supply from about 100 to about 1000 or more parts by weight of compound per million parts of ultimate treating composition. When the germinant seeds and emerging seedlings of many terrestrial plant species are contacted with compositions containing one of the oxirane compounds in dosages sufficient to supply from about 1.0 to about 50.0 pounds of the compound per acre, a persistent inhibition of the growth of such seeds and seedlings is obtained.

In selective applications to plants and/or their habitats for the pre-emergent control of the germinant seeds and seedlings of many undesirable plants, especially those of small-seeded grasses in areas planted with the seeds of desired broadleaf plants or supporting the growth of such plants, compositions containing certain of the oxirane compounds in dosages of from about 0.03 to about 0.5 pounds or more of the oxirane compound per acre have been found satisfactory. The application of larger dosages to terrestrial plants and/or their habitats controls the growth of germinant seeds, of all types, including broadleaf plants, as well as grasses. In all selective applications, the exact dosage to be employed is dependent upon the resistance of the broadleaf crop plants or their seeds to the particular oxirane composition employed and related factors.

It has also been found that compositions employing certain of the oxirane compounds of dosages of from about 250 to about 4000 or more parts by weight per million parts of ultimate treating composition are effective in controlling the growth of the established plants of many plant species. In many instances, the application of the compositions containing certain oxirane compounds in dosages of from about 250 to about 1000 parts per million by weight per million parts of treating composition results in the selective post-emergent control of many undesirable plant species, especially those of small-seeded grasses in areas supporting the growth of the established plants of desired crop plants, e.g., cotton, corn, cultured rice and white winter wheat. In all selective operations, the exact dosage to be employed is dependent upon the resistance of the crop plants to the particular oxirane composition employed and other related factors apparent to those skilled in the art.

The application to plants, plant-parts and/or their habitats of a composition containing a growth-suppressing amount of an oxirane compound is essential and critical for the practice of the present invention. The exact dosage to be supplied by the composition in a given operation is dependent upon the fungal and plant species and the stage of growth and hardiness thereof as well as the plant part to be exposed to the pesticidal composition. Other factors, such as, for example, the weather conditions of temperature and moisture, the weathering action of sun and rain, the possibly the decomposition of the compositions and the oxirane compounds contained therein by the action of bacterial and other soil organisms which eventually frees the plant, plant part, and/or their habitats of the composition must also be considered. Thus, while the application of low amounts of active compounds per acre may be sufficient for good control of a light infestation of weeds growing under adverse conditions, applications of from 5 to 10 pounds or more of active compound per acre may be required for good control of a dense infestation of hardy weeds growing under favorable conditions.

Compositions comprising an oxirane compound and a liquid or solid carrier allow the growth-suppressing amount of the active agent to be mixed in such quantity of ultimate treating material that adequate coverage of all plants and plant-parts or adequate admixture with their habitats (e.g., soil) can be obtained. Good growth-suppressing results are obtained when employing a carrier material in relatively small, but effective amounts. Generally, however, the best results are obtained by employing either a suface-active dispersing agent, in an amount sufficient to emulsify the oxirane compound with water as a carrier, for example, an amount which represents from 0.1 to 15 percent, by weight, of the total treating material; or a finely divided carrier solid, in an amount which represents from 40 to 99.5 percent, by weight, of the total treating material.

The exact concentration of the oxirane compounds employed in the compositions for application to plants, plant-parts and/or their habitats is not critical and can vary considerably provided the required dosage of effective agent is supplied on the plant, plant-part and/or habitat treated. The concentration of the oxirane compound in liquid compositions employed to supply the desired dosage generally is from about 0.0001 to about 50 percent by weight, although concentrations as high as 90 percent by weight are sometimes conveniently employed. In finely divided solid carrier compositions, the concentration of the oxirane compound can be from 0.1 to 60 percent by weight. In compositions to be employed as concentrates, the oxirane compound can be present in a concentration of from 5 to 98 percent by weight.

The quantity of treating compositions to be applied can vary considerably provided that the required dosage of active ingredient is applied in sufficient of the finished composition to facilitate the distribution of the active agent on the plant or plant-part, or the penetration of the active agent in the plant habitat. The required amount of the active agent conveniently can be supplied per acre treated in from 10 to 27,000 gallons or more of the liquid carrier or in from 10 to 2,000 pounds of the finely divided solid carrier.

Liquid compositions containing the desired amount of active ingredient can be prepared by dissolving the oxirane compound in an organic liquid carrier or by dispersing the oxirane compound in water with or without the aid of a suitable surface-active dispersing agent such as an ionic or non-ionic emulsifying agent. Suitable organic liquid carriers include the agricultural spray oils and the petroleum distillates such as diesel fuel, kerosene, fuel oil, naphthas and Stoddard solvent. Among the organic liquid carriers, the petroleum distillates are generally preferred. The aqueous compositions can contain one or more water immiscible solvents for the oxirane compound. In such compositions, the carrier comprises an aqueous emulsion, i.e., a mixture of water, emulsifying agent and water immiscible solvent. The choice of dispersing and emulsifying agent and the amount thereof employed is dictated by the nature of the composition and by the ability of the agent to facilitate the dispersion of the oxirane compound in the carrier to produce the desired composition. Dispersing and emulsifying agents which can be employed in the compositions include the condensation products of alkylene oxides with phenols and organic acids, alkyl aryl sulfonates, polyoxyalkylene derivatives of sorbitan esters, complex ether alcohols, mahogany soaps, and the like.

In the preparation of dust compositions, the active ingredient is dispersed in and on a finely divided solid carrier such as clay, talc, chalk, gypsum, bentonite, fuller's earth, attapulgite, and the like. In such operation, the finely divided carrier is mechanically mixed or ground with the oxirane compound. Depending upon the proportion of ingredients, these dust compositions can be employed as concentrates and subsequently diluted with additional solid carrier or with liquid or solid surface-active dispersing agent to obtain the desired amount of active ingredient in a composition adapted to be employed for the suppression of the growth of the plants. Also, such dust compositions can be dispersed in water, preferably with the aid of a surface-active dispersing agent, to form spray mixtures.

Satisfactory results are obtained when the oxirane compositions are combined with other agricultural materials intended to be applied to plants, plant-parts, and/or their habitats. Such materials include fertilizers, fungicides, insecticides, soil conditioning agents, and the like.

When operating in accordance with the present invention, compositions containing growth-suppressing amounts of the oxirane compounds are applied to plants, plant-parts and/or their habitats in any convenient fashion. Applications to a plant habitat, e.g., soil, can be carried out by simply mixing with the habitat, such as by applying to the surface of soil and thereafter dragging or discing into the soil to the desired depth or by employing a liquid carrier to accomplish the penetration and impregnation. The application of spray and dust compositions to the surface of soil can be carried out by conventional methods, e.g., power dusters, boom and hand sprayers and spray dusters.

In a further method, the distribution of the oxirane compositions in soil can be accomplished by introducing the agent in the water employed to irrigate the soil. In such procedures, the amount of water can be varied with the porosity and water holding capacity of the soil to obtain a desired depth of distribution of the agent.

Other components of the habitat of a plant can be employed in the transfer of the agent of the present invention to a plant or plant part.

In addition, the present method also comprehends the employment of an aerosol composition containing an oxirane compound as an active compound. Such a composition is prepared according to conventional methods wherein the active ingredient is dispersed in a solvent, and the resultant dispersion mixed with a propellant in liquid state. Such variables as the paticular active ingredient to be used and the particular plant part to be treated will determine the identity of the solvent and the concentration of the active ingredient therein. Examples of suitable solvents are water, acetone, isopropanol, and 2-ethoxyethanol. Also, employment of the oxirane compound in pastes, gels, foams, invert emulsions, and the like, as well as pigmented or unpigmented pelleted solids is comprehended.

The following examples further illustrate the present invention.

EXAMPLE 34

Separate aqueous compositions containing 2-(m-bromophenyl)-2-(2,2,2-trichloroethyl)oxirane, 2-(p-chlorophenyl)-2-(2,2,2-trichloroethyl)oxirane, 2-(m-nitrophenyl)-2-(2,2,2-trichloroethyl)oxirane, and 2-(p-bromophenyl)-2-(2,2,2-trichloroethyl)oxirane were prepared as follows:

Four parts by weight of the compound, 0.08 part of sorbitan trioleate (Span 85), and 0.02 part of a sorbitan monooleate polyoxyethylene derivative (Tween 80) are dispersed in 40 milliliters of acetone to produce a concentrate composition in the form of a water-dispersible liquid containing the predetermined oxirane compound as the sole active agent.

A portion of each of these concentrate compositions were separately dispersed in portions of water to provide aqueous compositions, containing 0.44 pound of the oxirane compound per 100 gallons of ultimate aqueous mixture.

The aqueous compositions were then employed for the treatment of seed beds of good agricultural soil which had been prepared and seeded with the seeds of various grass species and broadleaf plants. The grass species included white winter wheat, cultured rice, pigweeds, crabgrass, cheat grass, wild oats, Johnson grass, barnyard grass and yellow foxtail; and the broadleaf plants included corn. In the treating operations, a predetermined quantity of each of the compositions was applied to separate seedbeds as a soil drench at a rate of about 0.43 acre inch of aqueous composition per acre. The quantities were controlled to supply a substantial uniform dosage in a seedbed equivalent to 1.0, 2.0 and 5.0 pounds of the oxirane compound per acre. These dosages correspond, respectively, to a concentration, within the soil depth penetrated of about 1.6, 3.2 and 8.0 parts by weight of the oxirane compound per million parts by weight of soil. Other seedbeds were similarly seeded with the named plant species but were left untreated to serve as checks.

After about 2 weeks the seedbeds were examined to acertain what control of the growth of seeds had been obtained. The results are set forth in the following Table II.

Table II

| | Percent Pre-Emergent Control of Seed Germination at Various Indicated Toxicant Concentrations (in Pounds per Surface Area) | | | | | | | | | | | |
|---|---|---|---|---|---|---|---|---|---|---|---|---|
| Seed Species | 2-(m-bromophenyl)-2-(2,2,2-trichloroethyl)oxirane | | | 2-(p-bromophenyl)-2-(2,2,2-trichloroethyl)oxirane | | | 2-(m-nitrophenyl)-2-(2,2,2-trichloroethyl)oxirane | | | 2-(p-chlorophenyl)-2-(2,2,2-trichloroethyl)oxirane | | |
| | 1.0 | 2.0 | 5.0 | 1.0 | 2.0 | 5.0 | 1.0 | 2.0 | 5.0 | 1.0 | 2.0 | 5.0 |
| 1. Pigweeds | 95 | 100 | 100 | 50 | 50 | 90 | 85 | 95 | 95 | 50 | 100 | 100 |
| 2. Crabgrass | 0 | 100 | 100 | 0 | 100 | 100 | 95 | 100 | 100 | 95 | 100 | 100 |
| 3. Johnson Grass | 95 | 95 | 100 | 95 | 95 | 95 | 70 | 85 | 95 | 95 | 100 | 100 |
| 4. Barnyard Grass | 95 | 95 | 95 | 95 | 95 | 95 | 50 | 50 | 95 | 95 | 100 | 100 |
| 5. Wild Oats | 100 | 100 | 100 | 95 | 95 | 90 | 40 | 50 | 80 | 100 | 100 | 100 |
| 6. Cheat Grass | — | — | — | — | — | — | 80 | 100 | — | — | — | — |
| 7. Cultured Rice | — | 100 | 100 | — | 100 | 100 | 100 | 95 | 100 | 100 | 100 | — |
| 8. Yellow Foxtail | 100 | 100 | 95 | 0 | 0 | 80 | 100 | — | — | 95 | 95 | 95 |

Table II-continued

| | Percent Pre-Emergent Control of Seed Germination at Various Indicated Toxicant Concentrations (in Pounds per Surface Area) | | | | | | | | | | |
|---|---|---|---|---|---|---|---|---|---|---|---|
| Seed Species | 2-(m-bromophenyl)--2-(2,2,2-trichloro-ethyl)oxirane | | | 2-(p-bromophenyl)--2-(2,2,2-trichloro-ethyl)oxirane | | | 2-(m-nitrophenyl)--2-(2,2,2-trichloro-ethyl)oxirane | | | 2-(p-chlorophenyl)--2-(2,2,2-trichloro-ethyl)oxirane | | |
| 9. White Winter Wheat | 100 | 100 | 100 | 95 | 95 | 95 | 95 | 50 | 95 | 95 | 100 | 100 |
| 10. Corn | 30 | 95 | 95 | 0 | 50 | 95 | 100 | 50 | 0 | 85 | 95 | 95 |

At the time of the observations, the check areas showed populous and vigorous growing stands of the named plant species.

EXAMPLE 35

Aqueous compositions containing one of each of the following compounds:
2-(m-tolyl)-2-(2,2,2-trichloroethyl)oxirane;
2-(m-methoxyphenyl)-2-(2,2,2-trichloroethyl)oxirane;
2-(m-chlorophenyl)-2-(2,2,2-trichloroethyl)oxirane;
2-(m-fluorophenyl)-2-(2,2,2-trichloroethyl)oxirane;
2-(3,4-dichlorophenyl)-2-(2,2,2-trichloroethyl)oxirane;
2-(m-ethoxyphenyl)-2-(2,2,2-trichloroethyl)oxirane; and
2-(m-(benzyloxy)phenyl)-2-(2,2,2-trichloroethyl)oxirane
were prepared as in Example 34 and similarly employed for the pre-emergence treatment of various plant species.

As a result of such operations, it was found that the 2-(m-tolyl)-2-(2,2,2-trichloroethyl)oxirane compound gave substantially complete control of pigweeds, crabgrass, Johnson grass, barnyard grass, wild oats and yellow foxtail when the seeds of such species were contacted with compositions containing the active compound in amounts sufficient to supply a dosage of 2.0 pounds per acre.

In other similar operations, the 2-(m-methoxyphenyl)-2-(2,2,2-trichloroethyl)oxirane compound gave substantially complete pre-emergence control of pigweeds, crabgrass, Johnson grass and barnyard grass and the 2-(m-ethoxyphenyl)-2-(2,2,2-trichloroethyl)oxirane compound gave substantially complete control of crabgrass, Johnson grass, barnyard grass and wild oats when the seeds of such plant species were contacted with compositions containing the respective active compounds in amounts sufficient to supply a dosage of 2.0 pounds per acre.

In further pre-emergence operations, the 2-(m-(benzyloxy)phenyl)-2-(2,2,2-trichloroethyl) oxirane compound gave substantially complete control of pigweed, crabgrass, barnyard grass, wild oats and yellow foxtail when the seeds of such species were contacted with sufficient composition to supply a dosage of 20 pounds per acre.

The treatment of the seeds of pigweeds, crabgrass, Johnson grass and wild oats with a composition containing the 2-(3,4-dichlorophenyl)-2-(2,2,2-trichloroethyl)-oxirane compound at a rate of 2.0 pounds per acre likewise gave substantially complete control of the species.

Substantially complete pre-emergence control of crabgrass, Johnson grass, barnyard grass, wild oats and yellow foxtail was also obtained by the application of compositions containing 2-(m-chlorophenyl)-2-(2,2,2-trichloroethyl)oxirane and 2-(m-fluorophenyl)-2-(2,2,2-trichloroethyl)oxirane, respectively, at dosage rates of 0.25 and 0.5 pounds per acre, respectively.

EXAMPLE 36

Separate aqueous compositions containing the 2-(m-chlorophenyl)-2-(2,2,2-trichloroethyl)oxirane (Cmpd. A) and 2-(m-bromophenyl)-2-(2,2,2-trichloroethyl)oxirane (Cmpd. C) compounds of the present invention were prepared as in Example 34 for comparative pre-emergence herbicide tests against noxious grass species with the known 2-(p-chlorophenyl)-2-(2,2,2-trichloroethyl)oxirane (Cmpd. B) compound and 2-(p-bromophenyl)-2-(2,2,2-trichloroethyl)oxirane (Cmpd. D). The pre-emergence tests were conducted as in Example 34 and the results of such tests are set forth below in Table III.

Table III

| Cmpd. | Rate Lb/Acre | % Control | | |
|---|---|---|---|---|
| | | Water-Grass | Crab Grass | Johnson Grass |
| A | 1. 1/8 | 90 | 100 | 100 |
| | 2. 1/16 | 85 | 100 | 100 |
| B | 1. 1/8 | 90 | 20 | 30 |
| | 2. 1/16 | 60 | 0 | 0 |
| C | 1. 1/8 | 95 | 95 | 95 |
| | 2. 1/16 | 90 | 70 | 95 |
| D | 1. 1/8 | 60 | 0 | 25 |
| | 2. 1/16 | 30 | 0 | 0 |

At the same low dosage rates as set forth in the above table, no pre-emergence effect on the seeds of cotton and corn plants was observed.

EXAMPLE 37

An aqueous composition containing 2-(α,α,α-trifluoro-m-tolyl)-2-(2,2,2-trichloroethyl)oxirane was prepared as described in Example 34. The composition was then employed according to the procedures of Example 34 except that lower concentrations of the oxirane compound were employed in the composition.

The percent control of the various plant species at the employed dosage rate of the 2-(α,α,α-trifluoro-m-tolyl)-2-(2,2,2-trichloroethyl) supplied by the composition is set forth in the following Table IV.

Table IV

| | Percent Pre-Emergent Control of Seed Germination at Various Indicated Concentrations (in Pounds per Surface Area) | | | | | |
|---|---|---|---|---|---|---|
| Seed Species | 0.03 | 0.07 | 0.13 | 0.25 | 0.5 | 1.0 |
| 1. Pigweeds | 0 | 30 | 50 | 100 | 100 | 100 |

Table IV-continued

| Seed Species | Percent Pre-Emergent Control of Seed Germination at Various Indicated Concentrations (in Pounds per Surface Area) | | | | | |
|---|---|---|---|---|---|---|
| | 0.03 | 0.07 | 0.13 | 0.25 | 0.5 | 1.0 |
| 2. Crabgrass | 60 | 75 | 100 | 100 | 100 | 100 |
| 3. Johnson Grass | 0 | 80 | 100 | 100 | 100 | 100 |
| 4. Barnyard Grass | 50 | 95 | 95 | 95 | 95 | 95 |
| 5. Wild Oats | 30 | 85 | 95 | 95 | 95 | 95 |
| 6. Yellow Foxtail | 30 | 0 | 95 | 100 | 100 | 100 |
| 7. Soybeans | 0 | 0 | 100 | 40 | 50 | 60 |
| 8. Cotton | 0 | 0 | 0 | 0 | 30 | 20 |
| 9. White Winter Wheat | 0 | 50 | 100 | 100 | 100 | 100 |
| 10. Corn | 0 | 0 | 0 | 90 | 95 | 95 |
| 11. Beans | 30 | 30 | 30 | 60 | 70 | 95 |
| 12. Cultured Rice | 0 | 30 | 100 | 100 | 100 | 100 |

At the time of the observations, the check areas showed populous and vigorous growing stands of the named plant species.

EXAMPLE 38

An aqueous composition containing 2-(m-bromophenyl)-2-(2,2,2-trichloroethyl)oxirane was prepared as described in Example 34. Separate portions of this composition were thereafter dispersed in a further quantity of water to prepare aqueous spray compositions containing 250, 500, 1000, 2000, and 4000 parts, respectively, of the compound per million parts by weight of ultimate treating composition. These compositions were applied as foliage sprays to various grass and broadleaf plant species, the plants being of 2 to 4 inches in height and growing in seed beds. The treatments were carried out with conventional spray equipment, the plants being sprayed to the point of run-off. Similar beds of the plant species were left untreated to serve as checks. After about two weeks, the beds were examined to ascertain what control of the growth of plants had been obtained. The plant species employed, together with the percent control obtained at the employed dosage rate of the composition is set forth in the following Table V.

Table V

| Seed Species | Percent Post-Emergent Control of Seed Germination at Various Indicated Concentrations | | | | |
|---|---|---|---|---|---|
| | 250 | 500 | 1000 | 2000 | 4000 |
| 1. Crabgrass | 30 | 65 | 95 | 95 | 95 |
| 2. Johnson Grass | 95 | 95 | 95 | 95 | 95 |
| 3. Barnyard Grass | 95 | 95 | 95 | 95 | 95 |
| 4. Yellow Foxtail | 40 | 95 | 95 | 95 | 95 |
| 5. Soybean | 30 | 30 | 50 | 75 | 85 |
| 6. Cotton | 0 | 0 | 50 | 50 | 65 |
| 7. White Winter Wheat | 0 | 0 | 50 | 50 | 50 |
| 8. Corn | 0 | 30 | 50 | 95 | 95 |
| 9. Pinto Beans | 50 | 50 | 50 | 75 | 75 |
| 10. Wild Oats | 50 | 70 | 85 | 85 | 95 |
| 11. Cultured Rice | 0 | 0 | 0 | 40 | 50 |

At the time of the observations, the check areas showed populous and vigorous growing stands of the named species.

EXAMPLE 39

Separate acetone compositions containing 100 and 500 parts, respectively, of each of 2-(p-nitrophenyl)-2-(2,2,2-trichloroethyl)oxirane and 2-(m-nitrophenyl)-2-(2,2,2-trichloroethyl)oxirane compounds per million parts by weight of ultimate mixture were prepared by dissolving a pre-determined amount of each of the above comounds in acetone to give the desired concentrations. The solutions were dispersed in melted nutrient agar to produce culture media for fungal plants. The agar solutions were poured into petri dished and allowed to solidify. The solidified agar surface in each petri dish was inoculated with one species of a fungal plant; the plants employed being Staphylococcus aureus, Candida albicans, Tichophton mentagrophytes, Bacillus subtilis, Aspergillus terreus, Candida pelliculosa, Pullularia pullulans, Mycobacterium phlei, Cephaloascus fragans and Aerobacter aerogenes.

The inoculation was carried out by applying droplets of a solution containing the fungal plants to the agar surfaces. The inoculated petri dishes were then incubated for an appropriate period of time and under conditions conducive to the growth of the fungal plants involved.

After incubation, the petri dishes were examined to determine the degree of control of the fungal plants. In these operations, it was found that the composition containing 100 parts per million by weight of the 2-(p-nitrophenyl)-2-(2,2,2-trichloroethyl)oxirane compound gave complete control and kill of Bacillus subtilis and Aerobacter aerogenes. The composition containing 500 parts by weight of 2-(m-nitrophenyl)-2-(2,2,2-trichloroethyl)oxirane gave complete control and kill of Staphylococcus aureus, Candida albicans, Trichophton mentagrophytes, Bacillus subtilis, Aspergillus terreus, Candida pelliculosa, Pullularia pullulans, Mycobacterium phlei and Cephaloascus fragans.

In similar operations, it was found that compositions containing 500 parts per million by weight of composition of one of each of the following compounds:

2-(m-tolyl)-2-(2,2,2-trichloroethyl)oxirane; 2-(m-methoxyphenyl)-2-(2,2,2-trichloroethyl)oxirane; 2-(m-chlorophenyl)-2-(2,2,2-trichloroethyl)oxirane; 2-(m-fluorophenyl)-2-(2,2,2-trichloroethyl)oxirane; 2-(3,4-dichlorophenyl)-2-(2,2,2-trichloroethyl)oxirane; 2-(m-ethoxyphenyl)-2-(2,2,2-trichloroethyl)oxirane; 2-(m-(benzyloxy)phenyl)-2-(2,2,2-trichloroethyl)oxirane; 2-(p-chlorophenyl)-2-(2,2,2-trichloroethyl)oxirane; 2-(p-bromophenyl)-2-(2,2,2-trichloroethyl)oxirane; and 2-(m-bromophenyl)-2-(2,2,2-trichloroethyl)oxirane gave complete control and kill of Trichophyton mentagrophytes, Bacillus subtilis and Mycobacterium phlei.

What is claimed is:

1. A method for controlling undesirable plants which comprises applying thereto an effective herbicida amount of a substituted oxirane compound corresponding to the formula:

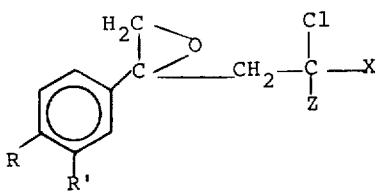

wherein X represents halogen; Z represents hydrogen, halogen, cyano or lower alkyl; R and R' each independently represent hydrogen, halogen, cyano, nitro, alkoxy of from 1 to 4 carbon atoms, trifluoromethyl, benzyloxy or lower alkyl, with the proviso that when R' is hydrogen, R is other than hydrogen.

2. A method according to claim 1 wherein said oxirane compound is applied to soil containing seeds of undesired plants.

3. A method according to claim 1 wherein said oxirane compound is applied to established plants.

4. A method according to claim 1 wherein R is hydrogen.

5. A method according to claim 1 wherein R and R' each independently represent hydrogen, halogen, nitro, trifluoromethyl, lower alkoxy or lower alkyl, with the proviso that when R' is hydrogen, R is other than hydrogen.

6. A method according to claim 1 wherein R is hydrogen and R' is halogen or trifluoromethyl.

7. The method of claim 1 wherein the compound is 2-(m-nitrophenyl)-2-(2,2,2-trichloroethyl)oxirane.

8. The method of claim 1 wherein the compound is 2-(p-nitrophenyl)-2-(2,2,2-trichloroethyl)oxirane.

9. The method of claim 1 wherein the compound is 2-(α,α,α-trifluoro-m-tolyl)-2-(2,2,2-trichloroethyl)oxirane.

10. The method of claim 1 wherein the compound is 2-(m-bromophenyl)-2-(2,2,2-trichloroethyl)oxirane.

11. The method of claim 1 wherein the compound is 2-(p-bromophenyl)-2-(2,2,2-trichloroethyl)oxirane.

12. The method of claim 1 wherein the compound is 2-(m-chlorophenyl)-2-(2,2,2-trichloroethyl)oxirane.

13. The method of claim 1 wherein the compound is 2-(p-chlorophenyl)-2-(2,2,2-trichloroethyl)oxirane.

14. The method of claim 1 wherein the compound is 2-(m-fluorophenyl)-2-(2,2,2-trichloroethyl)oxirane.

15. The method of claim 1 wherein the compound is 2-(3,4-dichlorophenyl)-2-(2,2,2-trichloroethyl)oxirane.

16. The method of claim 1 wherein the compound is 2-(m-tolyl)-2-(2,2,2-trichloroethyl)oxirane.

17. The method of claim 1 wherein the compound is 2-(m-methoxyphenyl)-2-(2,2,2-trichloroethyl)oxirane.

18. The method of claim 1 wherein the compound is 2-(m-ethoxyphenyl)-2-(2,2,2-trichloroethyl)oxirane.

19. The method of claim 1 wherein the compound is 2-(m-(benzyloxy)phenyl)-2-(2,2,2-trichloroethyl)oxirane.

20. The method according to claim 1 wherein R and R' each independently represent hydrogen, halogen, trifluoromethyl or lower alkyl, with the proviso that when R' is hydrogen, R is other than hydrogen.

21. A method for the selective control of weedy grasses in the presence of desirable crops which comprises applying to soil containing desirable crops before the plants to be destroyed emerge in a concentration toxic to weedy grasses, but not toxic to desirable crops, a compound of the formula

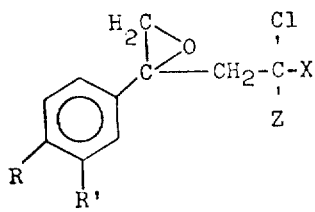

wherein X represents halogen; Z represents hydrogen, halogen, cyano or lower alkyl; R represents hydrogen and R' is halogen or trifluoromethyl.

22. The method of claim 21 wherein R' is halogen.

23. The method of claim 2 wherein the compound is 2-(m-chlorophenyl)-2-(2,2,2-trichloroethyl)oxirane.

24. The method of claim 21 wherein the compound is 2-(m-bromophenyl)-2-(2,2,2-trichloroethyl)oxirane.

25. The method of claim 21 wherein the compound is 2-(α,α,α-trifluoromethyl-m-tolyl)-2-(2,2,2-trichloroethyl)oxirane.

26. A herbicidal composition which comprises an inert carrier and as the active agent a herbicidally-effective amount of a compound of the formula:

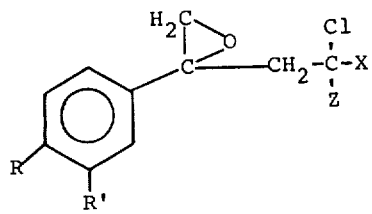

wherein X represents halogen; Z represents hydrogen, halogen, cyano or lower alkyl; R and R' each independently represent hydrogen, halogen, cyano, nitro, alkoxy of from 1 to 4 carbon atoms, trifluoromethyl, benzyloxy or lower alkyl, with the proviso that when R' is hydrogen, R is cyano, nitro, alkoxy, trifluoromethyl, benzyloxy or lower alkyl.

27. The composition of claim 26 wherein R represents hydrogen and R' represents halogen or trifluoromethyl.

28. The composition according to claim 26 wherein R and R' each independently represent hydrogen, halogen, trifluoromethyl or lower alkyl, with the proviso that when R' is hydrogen, R is other than hydrogen.

29. The composition of claim 26 wherein the compound is 2-(m-chlorophenyl)-2-(2,2,2-trichloroethyl)oxirane.

30. The composition of claim 26 wherein the compound is 2-(m-bromophenyl)-2-(2,2,2-trichloroethyl)oxirane.

31. The composition of claim 26 wherein the compound is 2-(α,α,α-trifluoromethyl-m-tolyl)-2-(2,2,2-trichloroethyl)oxirane.

32. Aqueous dispersion of the composition claimed in claim 26, the oxirane compound in such dispersion being present in a herbicidal amount of at least 0.0001 percent by weight.

33. The composition of claim 26 in intimate admixture with an inert finely divided solid, the oxirane compound in such admixture being present in a herbicidal amount of from 0.1 to 60 percent by weight.

* * * * *

UNITED STATES PATENT AND TRADEMARK OFFICE
CERTIFICATE OF CORRECTION

PATENT NO. : 3,930,835
DATED : January 6, 1976
INVENTOR(S) : Thomas M. Ozretich

It is certified that error appears in the above–identified patent and that said Letters Patent are hereby corrected as shown below:

Column 2, line 11, "where" should read --wherein--;

Column 4, line 46, "herbicical" should read --herbicidal--;

Column 5, line 32, the second "of" should read --in--;

Column 5, line 60, the second "the" should read --and--;

Column 5, line 66, "compounds" should read --compound--;

Column 6, line 37, "compositions" should read --composition--;

Columns 9 and 10, Table II-continued, under each of the last four headings, there should be subheadings as follows:
-- 1.0    2.0    5.0 --;

Column 11, line 68, "comounds" should read --compounds--;

Column 12, line 23, "dished" should read --dishes--;

Column 12, line 68, "herbicida" should read --herbicidal--;

Column 14, line 17, "2" should read --21--;

Column 14, line 47, "whrein" should read --wherein--.

Signed and Sealed this twenty-second Day of June 1976

[SEAL]

Attest:

RUTH C. MASON
*Attesting Officer*

C. MARSHALL DANN
*Commissioner of Patents and Trademarks*